(12) United States Patent
Baillie et al.

(10) Patent No.: US 11,583,653 B1
(45) Date of Patent: Feb. 21, 2023

(54) SAFETY COUPLERS FOR MEDICAL VENTILATOR SYSTEM

(71) Applicant: Percussionaire Corporation, Sandpoint, ID (US)

(72) Inventors: Mark John Baillie, Dover, ID (US); Shawn Adam Goughnour, Bonners Ferry, ID (US); Chad Thomas Nuxoll, Sandpoint, ID (US)

(73) Assignee: PERCUSSIONAIRE CORPORATION, Sandpoint, ID (US)

( * ) Notice: Subject to any disclaimer, the term of this patent is extended or adjusted under 35 U.S.C. 154(b) by 0 days.

(21) Appl. No.: 17/831,089

(22) Filed: Jun. 2, 2022

Related U.S. Application Data

(63) Continuation of application No. 17/697,518, filed on Mar. 17, 2022.

(51) Int. Cl.
*A61M 16/08* (2006.01)

(52) U.S. Cl.
CPC .... *A61M 16/0816* (2013.01); *A61M 16/0858* (2014.02)

(58) Field of Classification Search
CPC ........... A61B 5/08; A61B 5/082; A61B 5/087; A61M 11/06; A61M 16/0051; A61M 16/0057; A61M 16/0096; A61M 16/04; A61M 16/0488; A61M 16/06; A61M 16/0605; A61M 16/0666; A61M 16/0672; A61M 16/0677; A61M 16/0683; A61M 16/08; A61M 16/0808; A61M 16/0816; A61M 16/0825; A61M 16/0833; A61M 16/085; A61M 16/0858; A61M 16/0875; A61M 16/101; A61M 16/1045; A61M 16/105; A61M 16/1055; A61M 16/1065; A61M 16/107; A61M 16/1095; A61M 16/122; A61M 16/125; A61M 16/127; A61M 16/14; A61M 2016/0027;
(Continued)

(56) References Cited

U.S. PATENT DOCUMENTS 5,862,802 A 1/1999 Bird
6,571,794 B1* 6/2003 Hansen ............. A61M 16/0875
138/121

(Continued)

*Primary Examiner* — Annette Dixon
(74) *Attorney, Agent, or Firm* — Finch & Maloney PLLC

(57) ABSTRACT

Distinctly keyed male-female couplers are pneumatically connected to medical ventilator by distinct lines carrying pulsatile gas or sensory signals. Ventilator-mounted female coupler has entranceway cavity and larger receiving cavity delimited by catch edge. Male fence-forming longitudinal winglets extend from sealing plate carry terminal end convexities which latch onto catch edge. Winglets move inward due to larger fence circumference than entranceway and seat on catch. Winglets placed in tension due to locking length less than entranceway span, then convert force into sealing compressive force between sealing plate and female tube end. Conjoining male tube bayoneted and sheathed by projecting female tube, resulting in another gas seal. Two compressive seals formed between male distal port and pneumatic line. Extending male key(s) on winglet insertable into matching female slots. Convexities block insertion of non-matching couplers set due to interference by convexities on female on entranceway edges.

18 Claims, 10 Drawing Sheets

(58) Field of Classification Search
CPC ...... A61M 2016/003; A61M 2016/102; A61M 2039/1005; A61M 2039/1077; A61M 2039/1083; A61M 2202/0007; A61M 2202/0208; A61M 2202/0266; A61M 2202/0283; A61M 2205/0205; A61M 2205/0216; A61M 2205/0238; A61M 2205/14; A61M 2205/18; A61M 2205/183; A61M 2205/3368; A61M 2205/3569; A61M 2205/3592; A61M 2205/44; A61M 2205/50; A61M 2205/581; A61M 2205/582; A61M 2205/583; A61M 2205/584; A61M 2205/587; A61M 2205/6027; A61M 2205/6045; A61M 2205/6054; A61M 2205/6081; A61M 2205/8206; A61M 2206/10; A61M 2206/20; A61M 2206/22; A61M 2209/08; A61M 2209/088; A61M 2210/0618; A61M 2210/0625; A61M 2230/43; A61M 2230/432; A61M 39/1011; A61M 39/1055; A61M 39/223; A62B 7/14; A62B 9/02; B64D 2231/025; F16K 27/003; F16K 31/465; F16L 19/005; F16L 37/113; F16L 37/56; F16L 37/60; Y10T 137/598

See application file for complete search history.

(56) References Cited

U.S. PATENT DOCUMENTS

| | | |
|---|---|---|
| 6,581,600 B2 | 6/2003 | Bird |
| 6,595,203 B1 | 7/2003 | Bird |
| 8,347,883 B2 | 1/2013 | Bird |
| 10,737,049 B1 * | 8/2020 | Orr ................... A61M 16/0875 |
| 2020/0139076 A1 | 5/2020 | Baillie et al. |
| 2021/0299374 A1 | 9/2021 | Baillie et al. |
| 2021/0353159 A1 * | 11/2021 | Landis ................ A61M 16/107 |

* cited by examiner

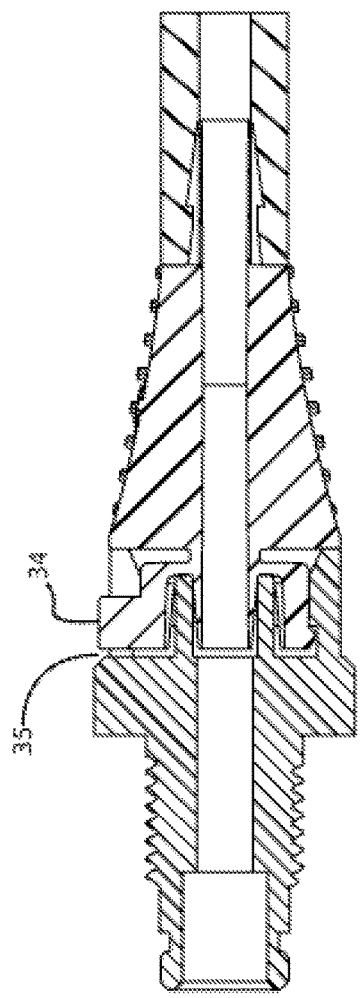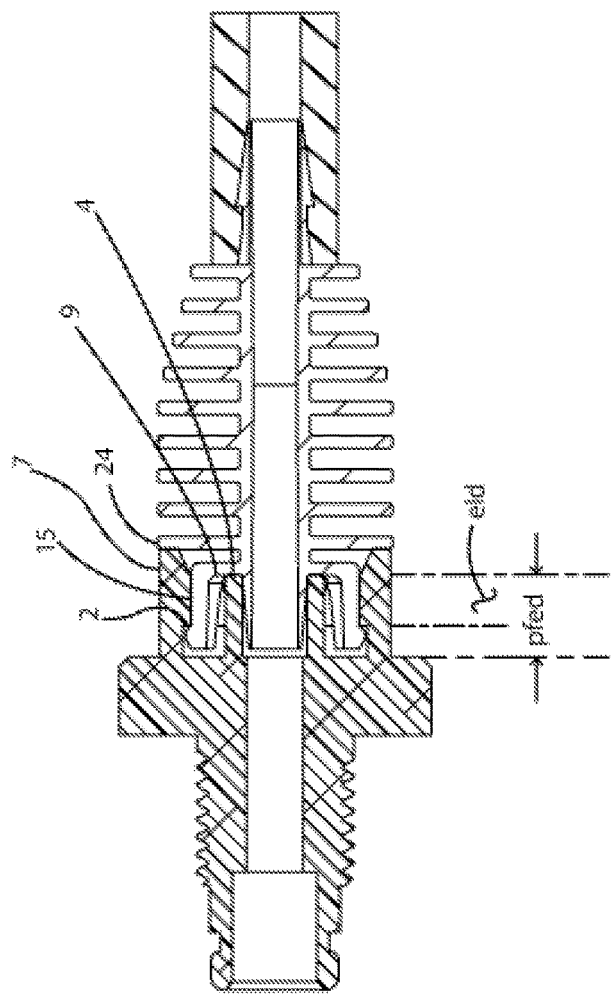

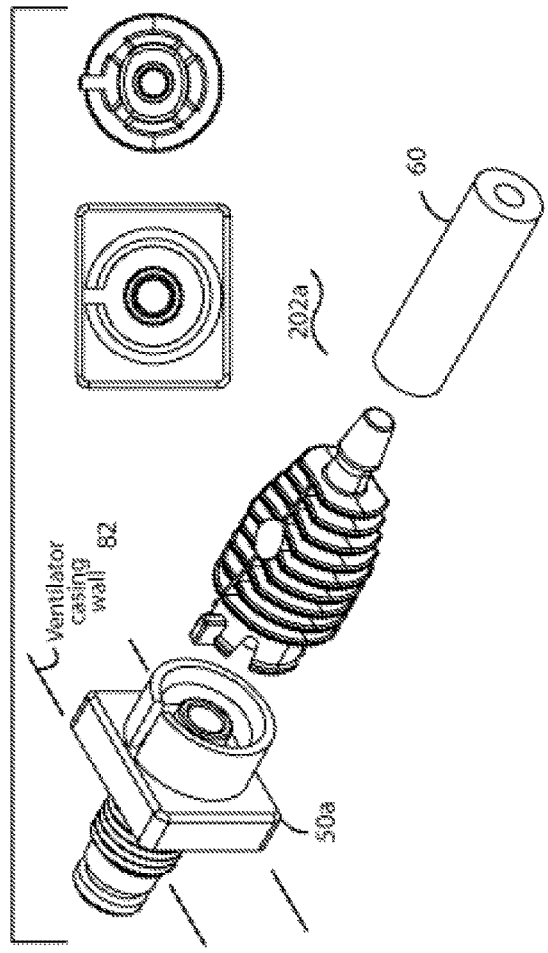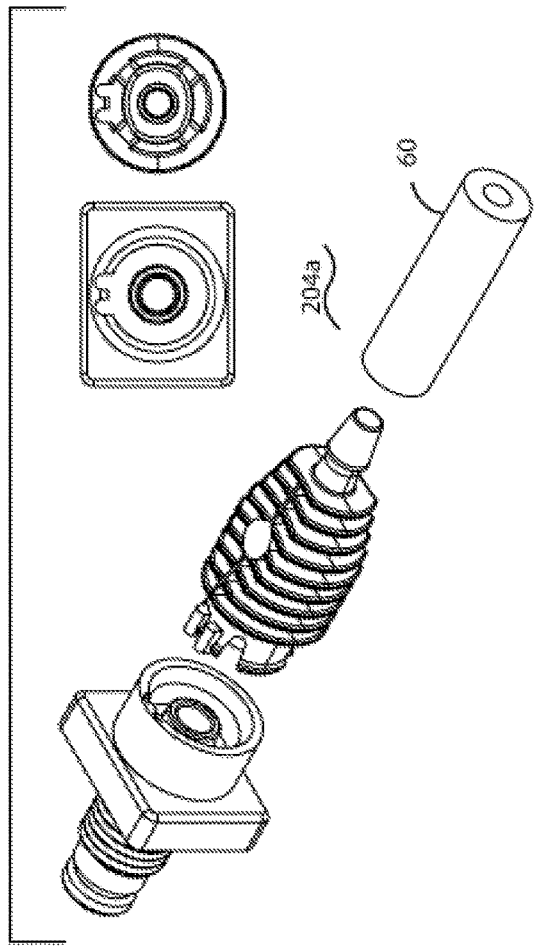

SAFETY COUPLERS FOR MEDICAL VENTILATOR SYSTEM

This is a continuation patent application based upon and claiming the benefit of Ser. No. 17/697,518, filed Mar. 17, 2022, now pending, the contents of which is incorporated herein by reference thereto. The present invention relates to a coupling system for connecting a ventilator to a pneumatic line or tube. The ventilator generates pulsatile gas at an internal pulsatile gas outlet, which is internal to the ventilator control and monitor casing, and senses sensory gas pressure P at a pneumatic sensory input, also internal to the ventilator casing. The female coupler body is mounted on the ventilator casing and pneumatically coupled to the ventilator's pulsatile gas outlet in one configuration, or, in a different configuration, the female coupler body, mounted on the ventilator casing, is pneumatically coupled to internal sensory gas pressure ventilator input. The made coupler is plugged into the female coupler. Pneumatic tubes or lines connect the ventilator to a breathing head via the coupler system.

BACKGROUND OF THE INVENTION

In healthcare clinics and facilities, ventilators are used in a variety of situations. Some ventilators are used as life-saving equipment to deliver pulsatile gas to a patient's airway to expand the patient's lungs and enhance oxygen flow into the lungs. Expiratory air flow from the patient must also be accounted for by the ventilator and breathing head. In other situations, intermittent rather than continuous pulsatile gas flow is supplied to the patient undergoing respiratory therapy. Examples of respirator systems can be found in U.S. Pat. Nos. 5,862,802; 6,595,203; 8,347,883 and U.S. Patent Publication No. 202000139076.

In both the life-saving situation and the therapeutic setting, it is critical that the operator correctly attach the pulsatile gas supply line to the pulsatile gas input on the breathing head, which breathing head is pneumatically connected to the patient's airway. Another critical connection to be made by the operator is the pressure sensory gas line between the breathing head and the ventilator. The sensory gas line enables the ventilator to determine, as a feedback signal displayed to the clinician, the gas pressure at the breathing head. Although color-coded pneumatic connecting lines and similarly color-coded ports on the ventilator casing reduce improper gas line connection errors between the ventilator and the breathing head, a unique male-female coupling system greatly reduces the probability of operator connecting error.

SUMMARY OF THE INVENTION

It is an object of the present invention provide an interlocking male and female coupler system wherein the pulsatile gas line male coupler can only be interlocked with the installed female pulsatile gas line fixture mounted on the ventilator casing. In a similar manner when the sensory gas line is to be coupled to the sensory gas port of the ventilator, a different unique male to female coupler is used, thereby avoiding operator error of misconnecting the supply line to the sensory line.

It is another object of the invention to provide the female coupler with an internal longitudinal gas passageway, and outboard exterior facing female port end and an interior ventilator female port which is interior to and pneumatically coupled to either the pulsatile gas outlet (if this female coupler is designated as a pulsatile gas port) or a sensory gas pressure ventilator input (if the female coupler designated a sensory gas pressure input).

It is an additional object of the present invention to form female receiving cavities in a female receiving wall. An exterior facing female edge on the female coupler includes, in one embodiment, a radially widening sloped transitional edge which forms an exposed external edge for the female receiving cavity. In a further embodiment, the female receiving wall has first and second circumferential grooves wherein a first groove forms a radially narrow circumferential cavity having an entranceway circumference and an entranceway longitudinal span. The second circumferential groove forms a radially larger circumferential cavity and the first and second circumferential cavities are defined and bounded by a delimiting edge.

In another embodiment, the male coupler has a proximal coupler end, facing the ventilator, and a distal coupler facing away from the ventilator. The male coupler body has a frustoconical primary outboard port male seal formed at the distal end of a male gas passageway. The male coupler body also has a frustoconical secondary outboard port male seal. This secondary outboard port seal is longitudinally inboard the primary outboard port male seal. These two outboard port male seals pneumatically connect the pneumatic line or to the gas carrying male passageway.

In a further enhanced embodiment, the male coupler has a projecting bayonet insertion tube terminating at the proximal male coupler end as an extension of the male gas passageway. The bayonet tube is sized to sheathe within a protecting female tube end of the female coupler. The male coupler body has radial or lateral sealing plate (lateral being normal to the bayonet tube axial centerline), sometimes identified as a sealing end plate wall of the male receiving cavity created by a coupled system. The male coupler has a plurality of spaced apart arcuate winglets which longitudinally extend from the sealing plate to the proximal male port end. The plurality of winglets form a male fence and, when coupled, form a male receiving cavity, The male fence in one embodiment is a cylindrical fence. In some situations, the winglets are circumferentially spaced apart. In other situations, the male winglets are laterally spaced from the axial centerline of the projecting bayonet insertion tube of the male coupler body. These winglets have an effective locking longitudinal winglet length which is less than the longitudinal entryway span of the female coupler. Further, the male fence formed by the winglets has a longitudinal fence depth. This longitudinal fence depth is less than the projecting female end of female coupler.

A further enhancement of the invention includes the provision wherein each winglet has a plurality or number of radially outward leading-edge convexities or catch surfaces at the winglet's terminal end. In some situations, these winglets are arcuate. In other situations, the winglets are squared off. Sometimes, the convexities are referred to as catch surfaces and the winglets are referred to as grappling legs.

In a further embodiment, the winglets extend longitudinally from the radial or lateral sealing plate and the effective locking length of the winglets is defined between the convexities and the sealing plate. This plurality or number of winglets define a fenced circumference or simply a male fence which is greater than the entranceway circumference. The male coupler includes one or more radially extending key tabs and the key tabs extend from one or more of the winglets. The key tabs are collinear with the bayonet tube and the male fence in one embodiment. Sometimes, the winglets define a squared off or rectangular male fence, the winglets are laterally spaced from the bayonet tube and the winglets define a lateral span away from and spaced apart from the tube's axial centerline. The key tab or tabs are complementary to the key slot or slots in the female coupler.

Operationally, the winglets move radially inward due to the male fence span being greater than the entranceway circumference (or the lateral fence span being greater than the lateral receiving channel span). Upon coaction of the fence-forming convexities on the delimiting edge boundary between the narrow female cavity and larger female cavity, the winglets are placed in tension due to the effective locking length being less than the entranceway's span. As a result, this tension force is transmitted to the male's sealing plate forcing the female terminus edge of the projecting female end as a compressive force applied between terminus edge and against the radial or lateral sealing plate as the compressive force.

Although the foregoing general discussion of one embodiment of the present invention focuses on a number of circumferential and radial elements configured around the projecting male bayonet tube and the sheathing portion of the projecting female end portion, which is a pipe or tube, the coupling system may be configured laterally to achieve similar results obtaining the compression seal between the male bayonet to in the sheathing projecting female tube and the winglets forming the cylindrical fence. For example, the inner female receiving wall system could be a square or a rectangular or some other multi-faceted system other than the inner female receiving wall forming cylindrical entranceways and radially larger cylindrical cavities.

As an example, if the coupler system was configured as a square, the inner female receiving wall would, in a preferred embodiment, include first, second, third and fourth grooves having a lateral entranceway span with respect to an axial centerline through the projecting female end. In the lateral square system, the first, second, third and fourth grooves for the female entranceway are located on the interior first, second, third and fourth walls of the squared-off female coupler. On the male coupler, the winglets would extend longitudinally from a laterally extending sealing plate which is normal to the bayonet. Therefore, the winglets are laterally spaced from the axial centerline of the bayonet. In order to generate tension on the winglets, the plurality of winglets move laterally inward due to the fenced lateral span being greater than the female entranceway lateral span and, upon coaction of the plurality of catch surfaces chamfers on the delimiting edge, the winglets are placed in tension due to the effective winglet locking length being less than the female entranceway longitudinal span. This tension force is converted into a compression with the female terminus edge being placed in sealing compression against the lateral sealing plate due to the longitudinal fence depth being less than the projecting female end.

Additional enhancements include forming a primary pressure seal between the sheathed bayonet end and the projecting female end. The bayonet may have a frustoconical bayonet shape with a narrow bayonet terminus end.

Other embodiments of the invention include multiple key tabs cooperating with matching key slots wherein one of the matching key-key slot combinations are used for the pulsatile gas supply line, another of the key-key slot combinations are used for the gas sensory line. In this manner, blocking elements and edges prohibit a non-matching keyed male coupler to be inserted into a female coupler.

Although the invention, as illustrated and described herein, is not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

In the description of the embodiments of the present invention, unless otherwise specified, azimuth or positional relationships indicated by terms such as "up", "down", "left", "right", "inside", "outside", "front", "back", "head", "tail" and so on, are azimuth or positional relationships based on the drawings, which are only to facilitate description of the embodiments of the present invention and simplify the description, but not to indicate or imply that the devices or components must have a specific azimuth, or be constructed or operated in the specific azimuth, which thus cannot be understood as a limitation to the embodiments of the present invention. Furthermore, terms such as "first", "second", "third" and so on are only used for descriptive purposes, and cannot be construed as indicating or implying relative importance.

Also, in this document, the term "longitudinal" should be understood to mean in a direction corresponding to an elongated direction of either the male bayonet tube or the female sheathing tube portion. The term "lateral" should be understood to mean in a direction normal or perpendicular to the longitudinal direction. The term "proximal" generally refers to items closer to the ventilator casing than other referenced items.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

FIGS. 6A-6D also show winglet convexities ("WCs") and, more particularly, FIG. 6A shows 5 WCs and the bifurcation of the key carried winglet convexities; FIG. 6B shows 6 WCs and the trifurcation of the key carried WCs; FIG. 6C shows 4 WCs; and FIG. 6D shows 6 WCs;

FIGS. 7A and 7B respectively diagrammatically illustrate a cross-sectional view of the male key tab disposed in the female slot (FIG. 7A), and a cross-sectional view of male winglets captured by retaining inboard delimiting edges of the female coupler (FIG. 7B);

FIGS. 8A-8D diagrammatically illustrate perspective views of various male couplers with different key tab configurations, the corresponding end views of the complementary female coupler ends and male coupler ends, as well as the pneumatic line or tube carrying either the pulsatile gas or the sensor gas pressure; and, FIG. 9 diagrammatically illustrates ventilator 80, the breathing head 110, pneumatic lines 124, 126, 122, and nebulizer 120.

DETAILED DESCRIPTION

Figure 1:
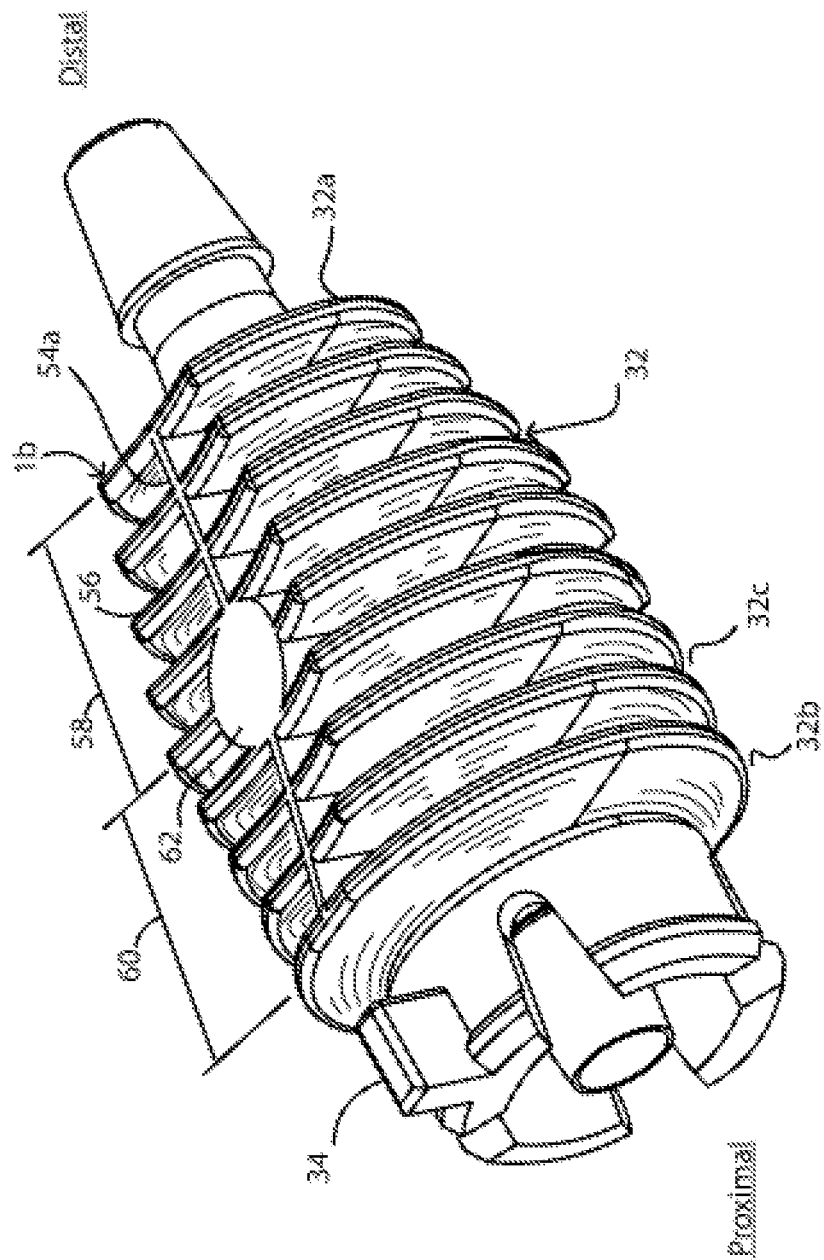
FIG. 1 diagrammatically illustrates a perspective view of the male coupler.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms. Similar numerals designate similar items in the drawings.

Figure 2:
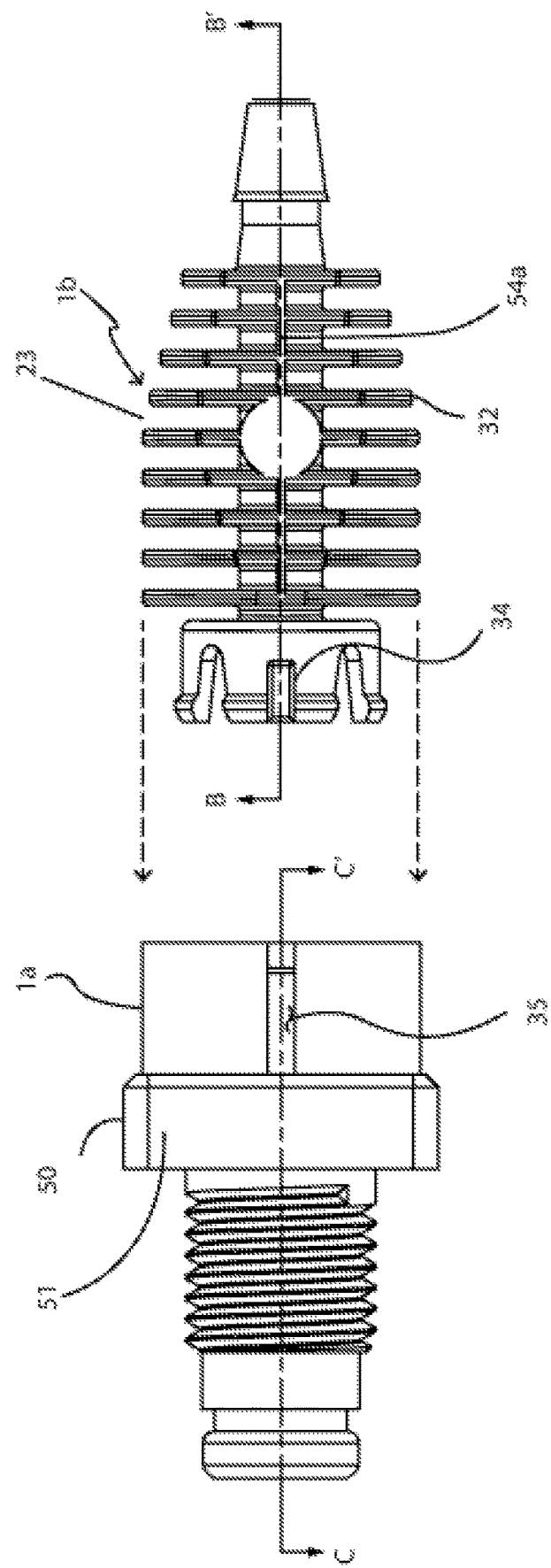
FIG. 2 diagrammatically illustrates the single key tab male coupler being insertable into the single key slot female coupler with alignment of the male key tab and the female slot.
Figure 3:
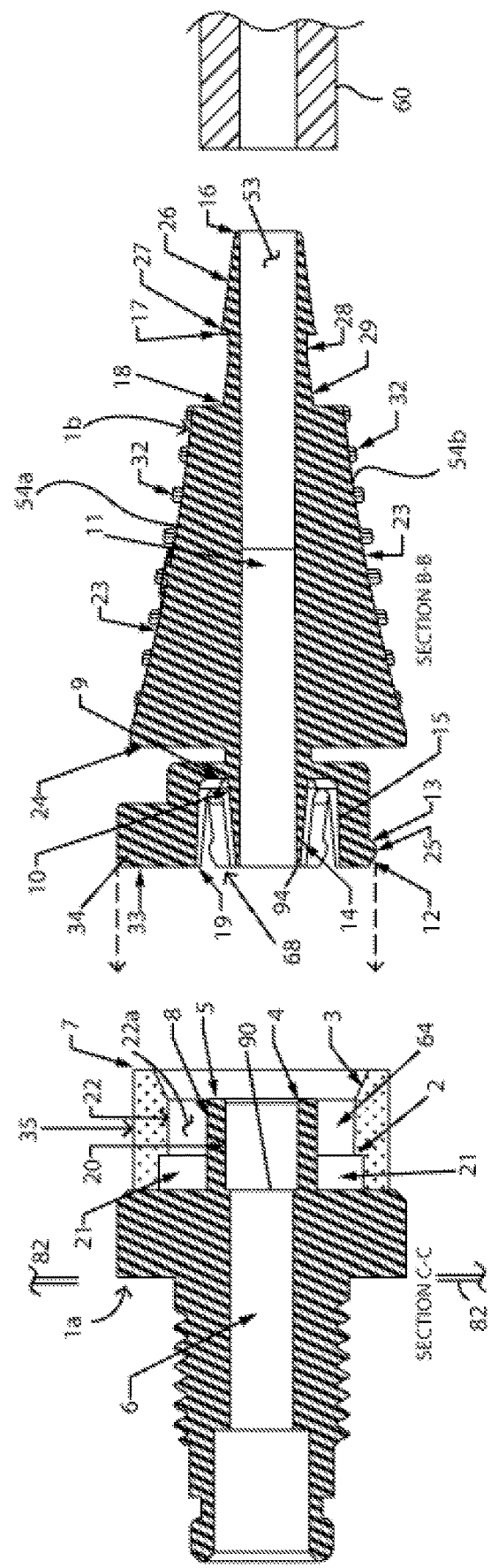
FIG. 3 diagrammatically illustrates details of the male coupler and the female coupler.
Figure 4:
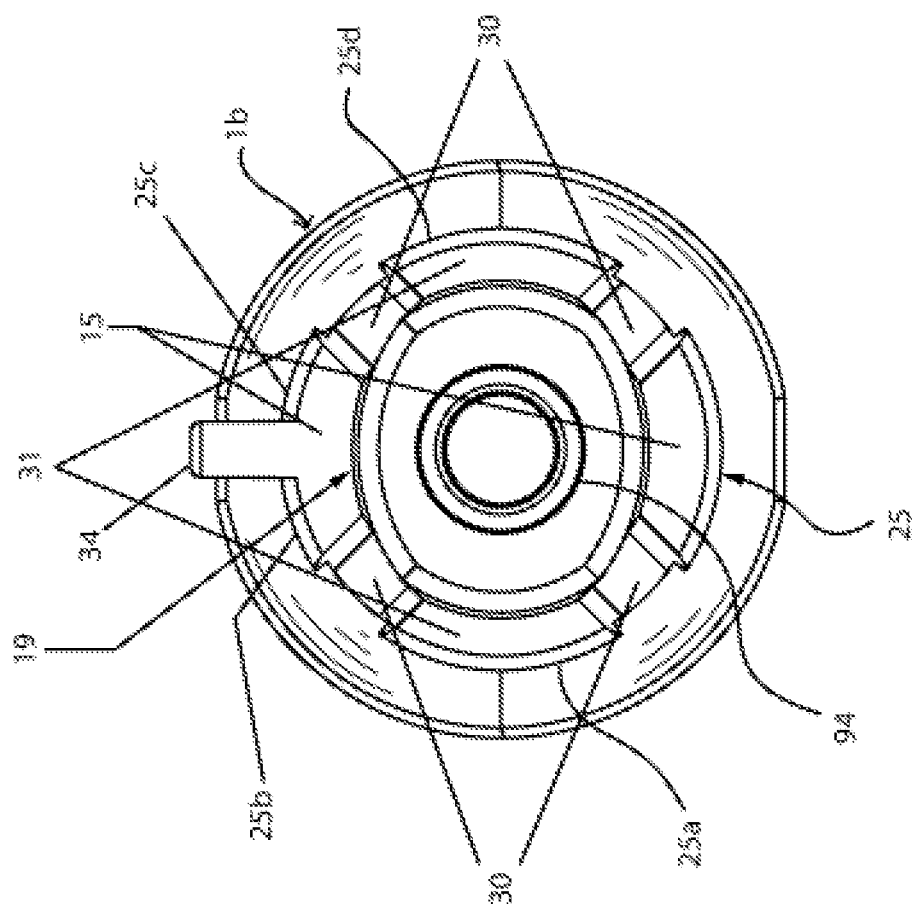
FIG. 4 diagrammatically illustrates an end view of the male coupler shown in FIG. 3.
Figure 8C:
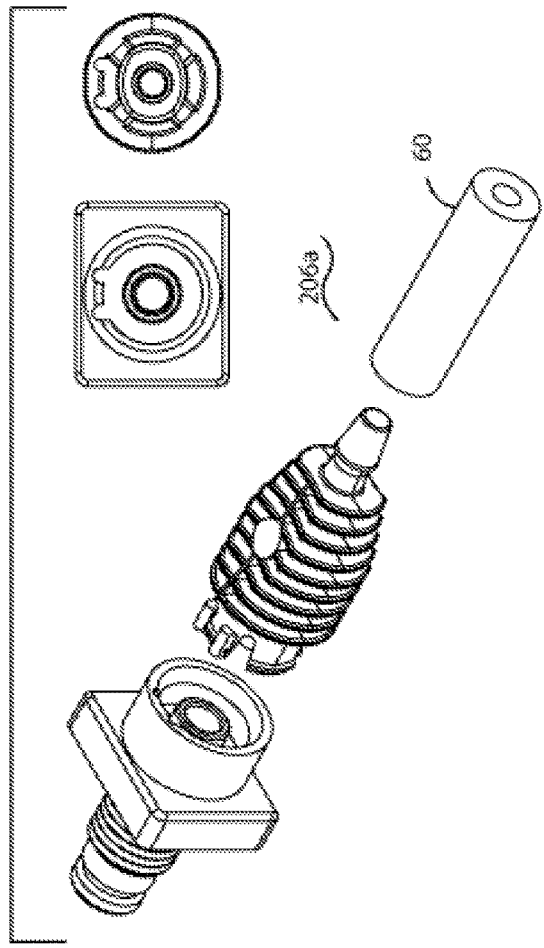
Figure 8D:
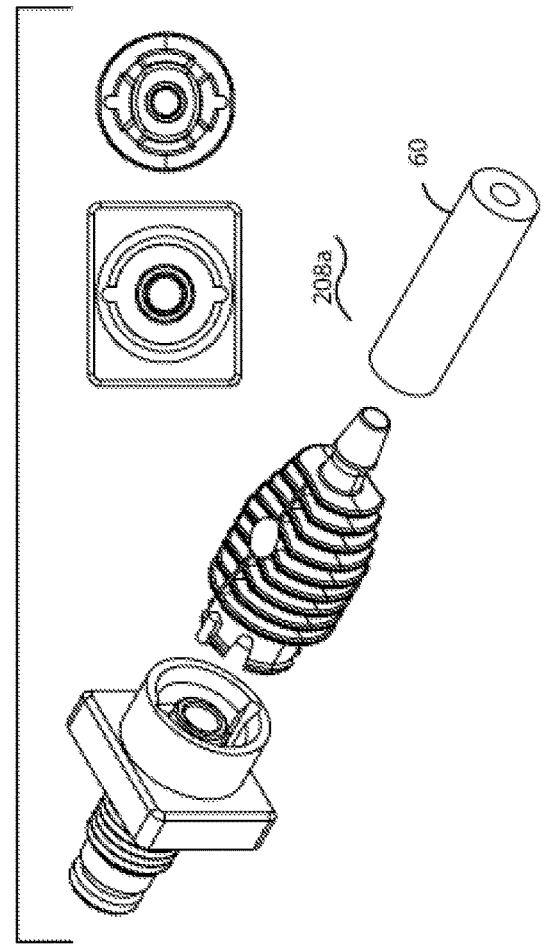

FIGS. 1, 2, 3, and 4 are discussed concurrently herein unless otherwise indicated. FIG. 1 diagrammatically illustrates a perspective view of the male coupler. FIG. 2 diagrammatically illustrates the single key tab male coupler being insertable into the single key slot female coupler with alignment of the male key tab and the female slot. FIG. 3 diagrammatically illustrates details of the male coupler and the female coupler. FIG. 4 diagrammatically illustrates an end view of the male coupler shown in FIG. 3. Throughout the description of the inventive coupler system, the term "proximal" is meant to refer to items closer to the bulkhead of ventilator controller and monitor 80. Ventilator bulkhead or wall 82 is diagrammatically shown in FIGS. 3, and 8A.

Figure 9:
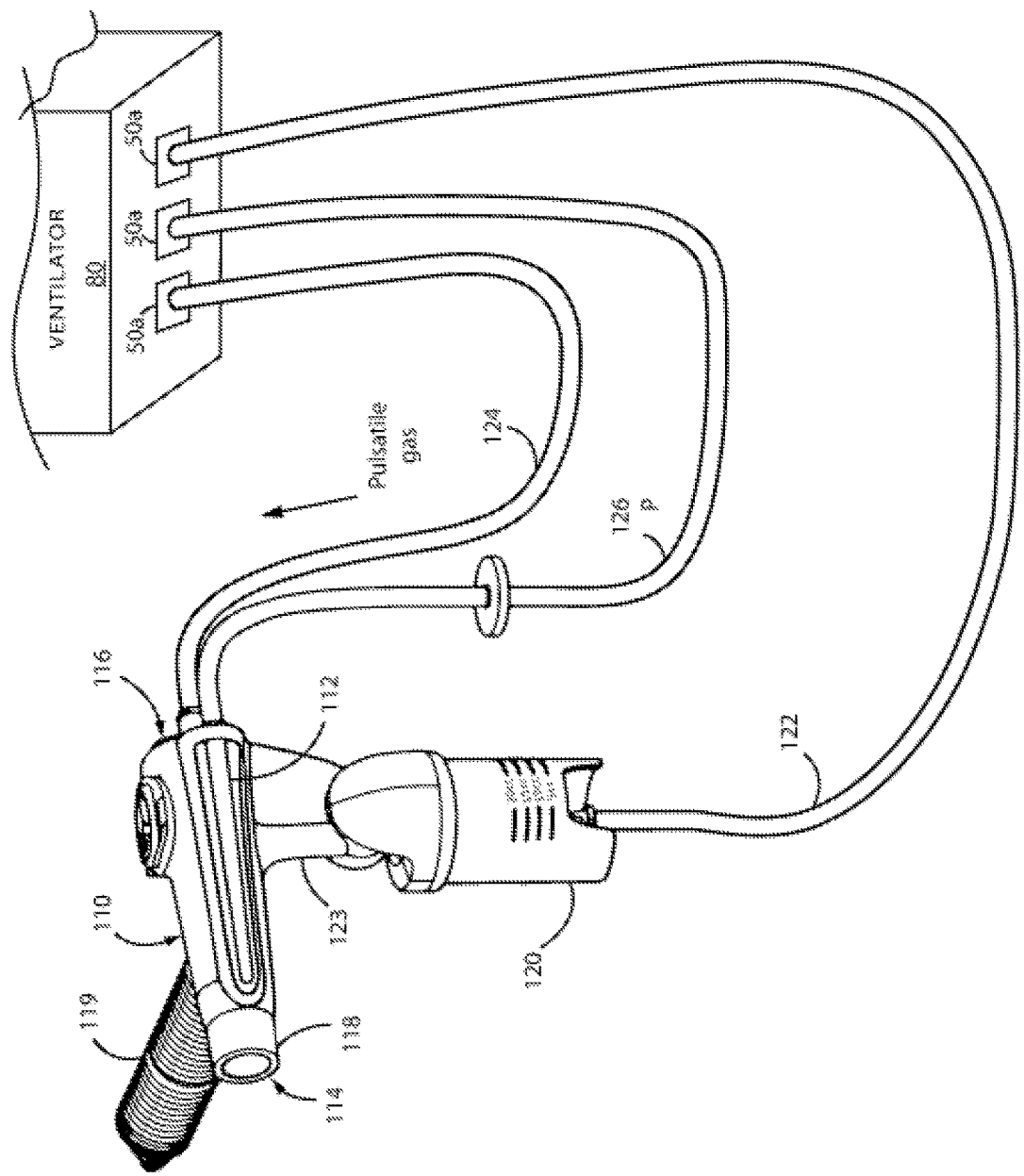

To understand the unique medical environment within which the inventive male and female coupler are deployed, FIG. 9 shows the ventilator system. FIG. 9 diagrammatically, also shows a number of squared-off exterior female coupler bodies 50a. FIG. 9 does not show details of the male and female couplers.

FIG. 9 diagrammatically illustrates breathing head 110 generally pneumatically coupled to ventilator 80. The ventilator operates as both a gas supply to breathing head 110 and as a control apparatus. In FIG. 9, a pulsatile gas supply line 124 is connected to an end cap at end 116 of breathing head 110 and is coupled, at the other end, to the ventilator gas supply control-monitor 80. Pneumatic sensory line 126 (carrying pressure P as a pneumatic sensory signal), is coupled at one end to a gas sensor port 153 on the breathing head 110 and is coupled, at the other end, to the ventilator monitor 80. Pneumatic sensory line 126 carries pressure signal P as a feedback signal to the ventilator which permits measurement of gas pressure in the breathing head 110. For further details of the operation of the breathing head 110, reference is made to patent application Ser. No. 16/391,481, filed Apr. 23, 2019, the contents of which is incorporated herein by reference thereto.

Figure 5:
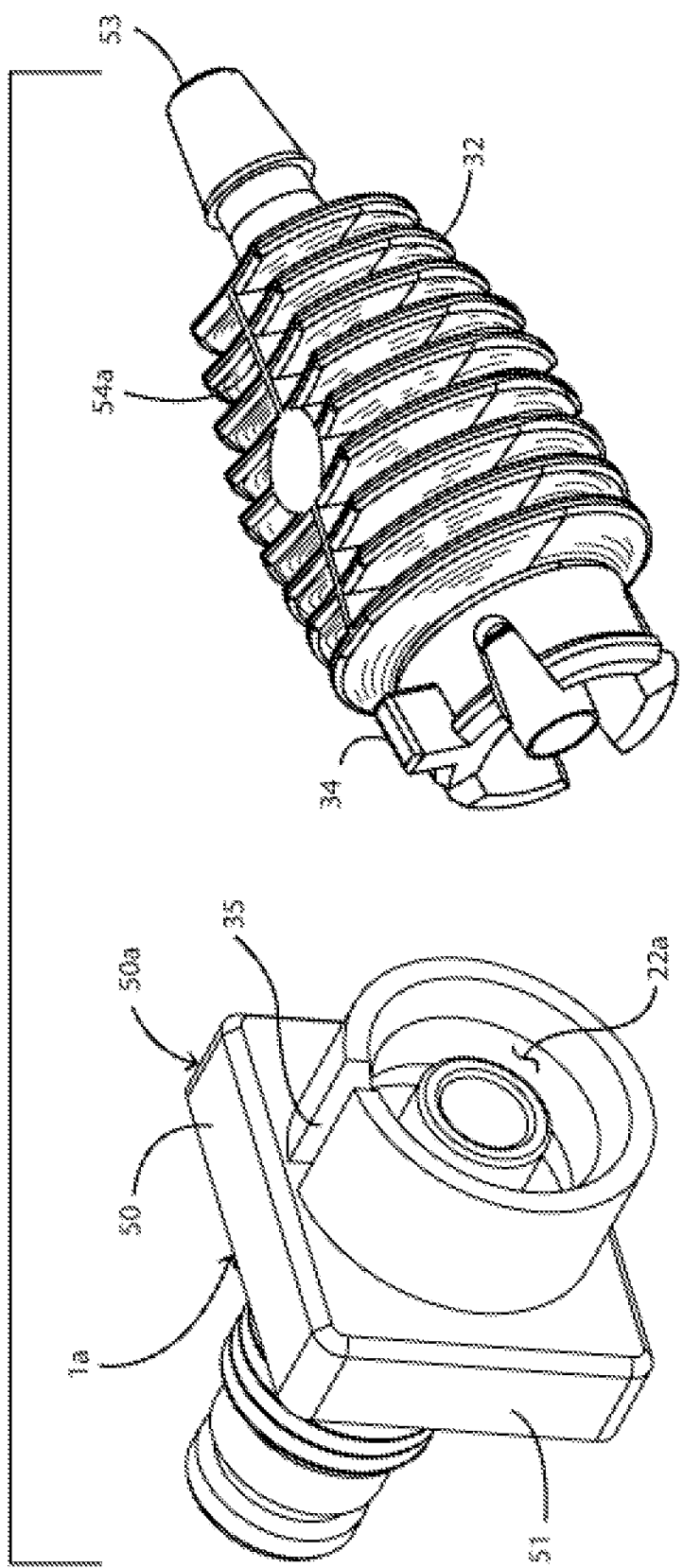
FIG. 5 diagrammatically illustrates a perspective view of the male and female coupler and the chamfer edges on winglets of the male coupler.

Referring now to FIGS. 1, 2, 3, and 4, the ventilator panel bulkhead female receptacle body coupler 1a (female coupler 1a) has exposed outboard extending projections (upper, lower, left and right projections 50, 51, see FIGS. 2, 5) forming a square 50a (see FIGS. 5 and 9). The outboard projections to allow for self-alignment and anti-rotation when multiple female couplers are installed adjacent each other on a ventilator panel bulkhead. When each female coupler receptacle has the same shape, the interlocking female coupler receptacles on the ventilator bulkhead prevent one another from rotating. FIG. 9 shows squared-off exposed outboard projections 50a on ventilator 80. Pneumatic lines 124, 126, 122 run from breathing head 110 to ventilator 80. A general discussion of the system is provided later in connection with FIG. 9. When several squared-off female couplers with outer body faces 50, 51 (see FIG. 2) are closely mounted on ventilator casing as shown in FIG. 9, each female coupler will not rotate due to the locking action of the square exterior walls 50, 51 of the closely mounted couplers.

Male coupler 1b defines an outboard port 53 (FIG. 3) defined by terminal end radii 16. Outboard port radii 16 provides a starting point to center and expand the pneumatic tube end 60 around slope 26 of outboard port 53. Slope 26, having a gradually increasing radii, gradually expands the tubing 60 to increase frictional attachment forces between the tube end 60 and outboard port 53. Slope 27 expands the tube end leading to a port defined high compression ring element 17 to form the primary seal at sealing region 28. Sealing region or area 28 is designed to form a relaxation area, longitudinally inboard of port opening 53 and ring element 17, for the tube end 60 to further increase the compression ring forces around edge 17. The longitudinally inboard sealing area and the radially extending compression ring element 17, forming a sharp transitional inboard edge, mitigates unintended detachment of tube 60 from male coupler 1b.

Outboard port 53 also includes a transitory further longitudinal inboard frustoconical slope 29 in safety seal region 28 (slope 29 being longitudinally inboard of transitory compression edge element 17), which again radially expands the tube end 60 forming a secondary compression seal between the tubing and outboard end 16. This secondary compression seal is important because (a) when tube 60 carries pulsatile gas from the ventilator 80 (see FIG. 9) to the breathing head 110, ultimately leading to the patient's airway, the maintenance of pulsatile gas pressure from the ventilator to the breathing head is critical, and (b) when tube 60 is configured as a pressure sensing line leading to the ventilator control-monitor 80 the pressure in sensory line 60 should be maintained to accurately provide a measurable gas pressure signal to the ventilator from the breathing head.

Further longitudinally inboard from seal region 28, the male coupler 1b defines a transitional radii 18 which radii defines the outboard region of stress risers 54a, 54b. These stress risers in the male coupler 1b prevent fatigue failures.

In practice as explained later, operators (primarily trained healthcare professionals) plug male coupler 1b into female coupler 1a. The female coupler is securely mounted on the ventilator control-monitor 80. See FIG. 9. The pulsatile pressure carrying tube is color coded and the color of the male and female couplers are similarly color coded to match the pulsatile pressure tube color. The breathing head also has color coded matched ports, identical to the color-coded couplers, to assure that the operator attaches the pulsatile pressure line to the pulsatile gas input port on the breathing head. An operator error arises if the pulsatile pressure line is incorrectly attached to a non-pulsatile gas port on the ventilator. Another operator error arises if the pulsatile pressure line is incorrectly attached to a non-pulsatile gas port on the breathing head. Similarly, if the pressure sensor tube or line is not connected at both ends to the sensor port on the ventilator and the sensor port on the breathing head, ventilator control over inhalation and exhalation gas is not properly monitored. For this reason, color-coding of ports on the ventilator side and on the breathing head side reduces, and possibly eliminates, line-switching operator error.

In practice, one breathing head is used by only one patient. The breathing head is delivered to the operator with disconnected pneumatic lines and the operator assembles the system (the breathing head plus the pneumatic lines) by attaching the lines to the head and then attaching the lines to the ventilator.

The operator should attach the correct pneumatic male coupler carrying line to the correct designated female coupler. Sometimes, the operator is provided with both a new, unused breathing head and a new, unused set of connecting tubes or lines. Therefore, in some instances, for each patient, the operator must accurately attach several lines from the ventilator to the breathing head. One critical line carries pulsatile gas to the breathing head and a second critical line carries the sensory pressure signal back from the breathing head to the ventilator. It is critical that gas pressure is maintained in each of these pneumatic lines. For the pulsatile gas supply line 124 leading to the breathing head 110 (FIG. 9), gas pressure and gas flow are most critical.

Since the ventilator control-monitor, generating the pulsatile gas and receiving pressure sensory signals on differentiated pneumatic lines, is typically stationary and the breathing head is highly mobile or movable compared to the stationary ventilator, these pneumatic lines are tugged (longitudinally acted upon), twisted (rotated) and bent (in the y and z axis away from the x longitudinal axis of the male coupler and the laid-out gas lines). Hence, the primary and secondary compression seals represent one of the several important features of the present invention.

Due to twisting and turning of the pneumatic lines or tubes, the male coupler is effected by the movement of the pneumatic lines. For this reason, male coupler 1b includes upper and lower stress risers 54a, 54b to prevent fatigue failures. The stress risers longitudinally span the interstitial space between the radial ribs 16. These stress risers 54a, 54b define longitudinal plates which in plane B-B' (FIG. 2) collinear with male interior passageway 11. FIG. 3 is a cross-sectional view of male coupler 1a from the perspective of line B-B' in FIG. 2. The plane B-B' is defined by the risers 54a, 54b. For purposes of discussion, the top of male coupler 1b and female coupler 1a is defined as the upper outboard region of primary male key tab 34. See FIGS. 1 and 5. In some embodiments, only a single longitudinal plate is disposed in the interstitial space between two adjacent radial fins. In one embodiment, the plane defined by risers 54a, 54b bisects primary key 34 and the plane passes through the longitudinal and axial centerline B-B' of the male coupler. In another embodiment, riser 54a is disposed at the zero (0) degrees through tab 34 (see FIG. 4) and the second riser is 90 degrees displaced from riser 54a.

It should be noted that it is not necessary that primary key 34 be positioned extending outboard from the top side of the male coupler. In other words, primary key 34 could be rotated to any radial position (in the range from 0 degrees to 360 degrees) with respect to the plane defined by the risers as long as the radial position of primary key 34 is complementary to the radial position of primary slot 35 in female coupler 1a as shown by the radial coincidence of the key tab and key slot in FIG. 2.

Figure 6A:
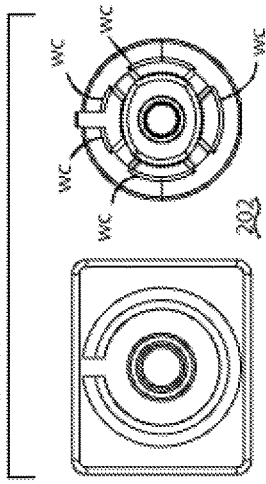
FIGS. 6A-6D diagrammatically illustrate end views of complementary male and female couplers respectively showing a single tab-slot configuration 202 (FIG. 6A); a two-tab closely set tab-slot configuration 204 (FIG. 6B); a spaced apart two-tab-slot configuration 206 (FIG. 6C); and an upper and lower opposing single tab-slot configuration 208 (FIG. 6D).
Figure 6B:
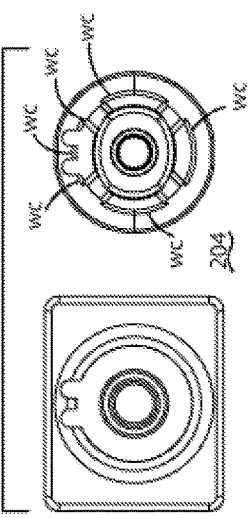
Figure 6C:
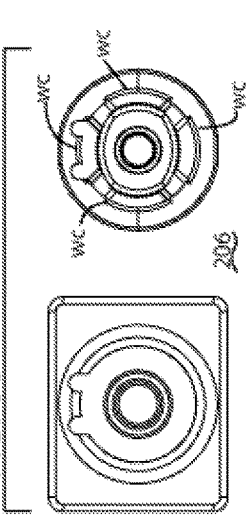
Figure 6D:
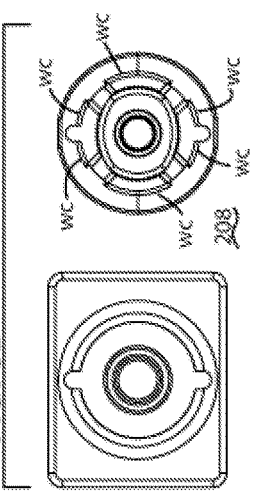

For example, FIGS. 6A-6D show single and multiple primary keys at different radial positions relative to the bisecting riser plane 54a, 54b. Stated otherwise, with respect to the preferred topside primary key extension, the manufacturer can select the radial position of the primary single key to be at any radial position from 0 degrees to 360 degrees. FIG. 6D shows a two primary key system with one key tab at the 0 degree topside position and the second primary key tab at the 180 degree position. The same holds true for the two key tab embodiments shown in FIGS. 6B, 6C, and the top and bottom two key embodiments shown in FIG. 6D.

FIGS. 6A-6D diagrammatically illustrate end views of complementary male and female couplers respectively showing: the single tab-slot configuration 202 (FIG. 6A); the two closely set tab-slot configuration 204 (FIG. 6B); the spaced apart two tab-slot configuration 206 (FIG. 6C); and the upper and lower opposing single tab-slot configuration 208 (FIG. 6D). FIGS. 6A-6D also show winglet convexities ("WCs") and, more particularly, FIG. 6A shows 5 WCs and the bifurcation of the key carried winglet convexities; FIG. 6B shows 6 WCs and the trifurcation of the key carried WCs; FIG. 6C shows 4 WCs; and FIG. 6D shows 6 WCs.

As shown in FIGS. 2, 5, key 34 is insertable into key slot 35. This major or primary key 34 is insertable into major or primary slot 35 which provides a complementary one-way coupling. There are several complementary primary and secondary control interfaces to assure that the operator couples the correct pneumatic lines to the correct female pressure ports on the ventilator control-monitor.

FIG. 1 shows male coupler 1b with a series of laterally extending, radial fins 32. The total circumferential span of this series of radial fins longitudinally changes such that the outboard-most fin 32a has a smaller circumference as compared to the proximal or inboard-most radial fin 32b, and in this embodiment, the intermediate fins have graduated circumferences such that the most adjacent fins to outboard fin 32a is slightly larger than fin 32a, the next series of fins (more longitudinally inboard from outer fin 32a) have gradually larger circumferences. The next to the last inboard fin is 32c slightly smaller than the inboard fin 32b. The presence of radial fins 32, as a group, is functional in that the radial fins, as a group, establish a mechanical stress relief for the male coupler. However, the individual fin shape and the overall fin system 58, 60 in FIG. 1 is ornamental. The stress relief fin set 32 could be configured (a) such that each fin, for example, fins 32a, 32b, and all intermediate fins could have the same circumference; or (b) each fin could have a peripheral edge which is formed by two opposing right angle (the preferred embodiment shows chamfers at each opposing longitudinal fin edge); or (c) the fin set 32 could have a first group of fins, each having the same small circumferential span, a second group of fins each having the same circumferential span but the second group having a larger circumferential span than the first group, and a third group of fins, each having the same larger circumferential span than the first and the second fin groups.

One of the several important aspects of the present invention is the use of a series, more than three, radial fins having a longitudinal span extending from the outboard double compression tube connection (generally defined by seal areas 28, 29 FIG. 3) to an inboard location near the base of the specially configured male key (predominated by primary key tab 34, FIG. 1). Although the fin series shown in the figures has several mechanical functional features discussed herein, there are many ornamental features which are not structurally needed to accomplish the stress relief of a three-fin or larger series. Some of the finer ornamental features are: the chamfer peripheral edge of each fin shown in FIG. 1; the continual graduated circumferential spans of the multi-fin system shown in FIG. 1; the continual graduated spans of the partial arcuate cut-out segments 56 on each fin; the increasing continual graduated spans of the partial arcuate cut-out segments 56 on first fin group 58 (FIG. 1) as compared with the decreasing continual graduated spans of the partial arcuate cut-out segments 56 on second fin group 58; and the central platform 62 on the middle fin. Further, the platform may be placed at any location on the radial fin set, that is, at the outboard-most location, at a central location, and at an inboard location. Also, the platform may be configured to longitudinally span all or a portion of the longitudinal span of the fin set rather than the three-fin platform span shown in the figures.

However, some partial arcuate cut-out segments 56 on each fin do provide a mechanical function which improves the use of the male coupler as explained below. FIG. 1 shows partial arcuate cut-out peripheral segments 56 forming, as a collection, an upper finger grip. In a preferred embodiment, male coupler has an upper finger grip formed by the series of partial arcuate cut-outs 56 and an opposing lower finger grip formed by the series of partial arcuate peripheral cut-outs. See generally FIG. 3. The upper and lower series of partial arcuate cut-outs form a concave region spanning regions 58 and 60 in FIG. 1.

The interstitial space 23 (FIG. 2, 3) between each rib, in addition to the series of concave partial arcuate cut-outs 56, is configured to cradle an operator's gloved fingers (one finger on the upper concave cut-out and the other finger on the lower concave cut-out), while allowing the excess material of the gloved finger to slightly penetrate the open or interstitial space in between the grip ribs 32 for an improved tactile response and to increase the gripping force during connection and removal of the male coupler to and from the female coupler. Finger grip ribs 32 also allow some flexing or flexion of the male coupler during use to reduce stress incurred when pneumatic lines or tubing apply transitional force to connector coupler system.

One of the several important aspects of the present invention is the multiple, one-way key system, with complementary interlocks and guide elements on the male and female couplers.

Each male coupler fitting (see FIGS. 6A-6D) has been designed with a unique key tab feature 34 (see FIG. 3, single topside key tab on male coupler 1b) to prevent connection with a non-similar panel bulkhead receptacle, female coupler 1a, key slot feature 35. Inboard edge 33 on the male coupler key tab has a unique key feature designed to contact the outer or outboard edge 7 on the female coupler or to engage sloped inner edge 3 on the female coupler which first prevents the start of insertion into a bulkhead unless the unique male key tab 34 matches unique female key slot 35 and the key tab is aligned with the key slot.

As shown in FIGS. 6A-6D, there are several combinations of primary male keys 34 which coact, mate, and are exclusively insertable into complementary female key slots. FIG. 6A shows the topside, primary key tab and also shows bifurcated winglet convexities, "WC," on either side of tab 34. FIG. 6B shows dual primary keys having two key tabs rotationally displaced from each other about 10 degrees apart, off the 0-degree coupler position and also shows an intermediate winglet convexity WC between these widely arcuately spaced apart key tabs and shows trifurcated winglet convexities or WCs. The dual key tabs in FIG. 6C are set apart about 10-15 degrees off the 0-degree coupler position and also shows an intermediate winglet convexity WC between these widely arcuately spaced apart key tabs. FIG. 6D shows a topside key tab and an opposing key tab at 180 degrees. Each key tab in FIG. 6D carries bifurcated winglet convexities. Hence, given the small size of the couplers (the male coupler being about 1 inch long, that is, having a longitudinal span of about 1 inch), there are several locational positions for the primary keys. The claims appended hereto are meant to cover these variable primary key sets (one on the male side and the second on the female side) forming a complementary interlocking system.

In order to explain primary and secondary blocking features of the present invention, reference will be made to the single primary topside key tab 34 male coupler and the single primary receiving key slot 35 female coupler shown in FIGS. 1, 2, 3, 4, 5, 6A, 7A, 7B and 8A. FIGS. 7A and 7B respectively diagrammatically illustrate a cross-sectional view of the male key tab disposed in the female slot (FIG. 7A), and male winglets captured by retaining inboard edges of the female coupler (FIG. 7B). The mechanical aspects discussed in connection with single topside key male coupler and single topside receiving key female coupler can be applied equally to the different key set systems shown in FIGS. 6A-6D (coupler sets 202a, 202b, 202c, and 202d) and 8A-8D (coupler and pneumatic line sets 202a, 202b, 202c, and 202d with tube or line 60), and also equally applied to primary key sets having three or more primary keys.

As explained below, one of the several important features of the present invention is the combination of the matching or complementary key sets with the pressure seals described herein below. Likewise, the secondary blocking and permissible secondary key sets can be employed with these various primary key configurations.

The secondary key subsystem, sometimes referred to as a blocking subset, is described herein. Returning to the single primary topside key tab 34 coupler and shown in FIGS. 1, 2, 3, 4, 5 and 7A and 7B, and, more particularly FIGS. 3 and 4, when the operator attempts to force a not matching key or unaligned male coupler 1b into the panel bulkhead female connector or coupler 1a, edge 19 of the secondary key winglet 15 actively prevents connection by jamming between edge 8 and the outboard facing edge of projecting female passage end wall 22 of the female coupler 1a (the panel bulkhead receptacle). As shown in FIG. 4, the male tab 34 bisects the convexities 25b, 25c which are present at the radially outer terminal end of tab 34 carrying winglet 15. Referring to FIG. 3, if a two key tab male coupler (FIG. 6B) was being inserted into a single slot female coupler 1a (FIG. 3), either winglet 25b or 25c (which bisect key tab 34) (FIG. 4) would block insertion of the inboard portions of male coupler into the female coupler because winglet edge 19 (FIG. 3) on the two-tab male coupler would be blocked by female edge 8 of the single slot female coupler 1a. Hence, winglet 15 on all the key-carrying winglets shown in FIG. 8A-8D, has a secondary blocking key set both limiting insertable access into a non-complementary female coupler, but also permitting access and insertion into a complementary female coupler.

Operationally, the male coupler fits into the female coupler in the following manner. On the female coupler, the radially inboard sloped female edge 3 provides centering and guidance for male chamfer edge 12 on the terminal proximal ends of positive retention winglets 15 and 31. Winglets 15 and 31 are defined as a circumferential fence on the male coupler. The leading-edge convexity element 25 of chamfer edge 12 is slightly radially angled outboard such that radial span of all chamfer edges (the five chamfer edges 25, 25a, 25b, 25c, and 25d, on winglets 15, 31 in FIG. 4) are slightly larger than the radial span of female receiving cavity 22, 64 shown in FIG. 3.

Stated otherwise, the cylindrical female receiving cavity has a radially widening sloped transitional female edge 3 (a frustoconical shaped edge 3) which leads to a radially narrow first circumferential groove forming an entranceway 64, 22 and further leading longitudinally inboard to a second circumferential groove forming region 21 on the female receiving cavity. Circumferential groove cavity 21 is longitudinally inboard of first circumferential groove entranceway 22, 64. A delimiting edge 2 defines the boundary between entranceway 64, 22 and radially larger second circumferential groove cavity 21.

The female coupler 1a has a cylindrical female receiving cavity. A projecting female end tube, defined by projecting tubular wall segment 20, projects into the radially inboard female receiving cavity 22a. The projecting female end tubular segment 20 is the extension of gas female passageway 6. The projecting female end segment 20 is coaxial with respect to the female receiving cavity 22a and, in the illustrated embodiment, coaxial with female gas passageway 6. The coaxial relationship of radially inboard female receiving wall 22a and the projecting female end segment 22a is important for mating and establishing the several gas pressure seals between female coupler and the male coupler. The projecting female end segment 20 has terminus end 4, which compressively seals against male cone 10.

And shown in FIG. 3, male coupler 1b has a male coupler body with a proximal male port end which is proximal to the exterior facing female coupler 1a and proximal to the ventilator casing wall 82. Male coupler 1b also has, on its right end, a distal male port end. Male coupler 1b as a longitudinal gas male passageway 11 in the illustrated embodiment. In all embodiments, without regard to the coaxial nature of gas passageway 11 and the proximal and distal male port ends, the proximal male port end is to be inserted by the operator into the ventilator-mounted female coupler and the distal male port end is to be connected by the manufacturer to a gas carrying tube or pneumatic line 60.

When leading edge convexity element 25 of winglets 15 and 31 are inserted into female cavity 22a, 64 and when convexity 25 transitions past female receiving cavity edge 3, the stress relieving arcuate gaps 30 of winglets 15, 31, shown in FIG. 4, allow winglets 15, 31 to move radially inward while female projecting tube end 20 aligns and centers within the male fence (that fence formed by the winglets 15, 31, and more particularly, the convexities 25, 25a, 25b, 25c and 25d on the terminal ends of the winglets). The result being alignment of the male projecting, bayonet wall end segment 14 with the projecting female tube end 20 resulting in the bayonetting of male tube or pipe 94 into female tube or pipe 20 and sheathing by the female pipe over the male pipe. As used herein, the terms "pipe", "tube" and "conduit" all refer to the same, generally rigid, gas carrying element.

The details of radially outboard protruding chamfer edges 12, shown in FIGS. 3, 4, are described herein. Each chamfered winglet edge carries at least one, and sometimes more than one, radially outboard extending convexity 25. Tab 34 extends radially outward from winglet 15) and longitudinally spans a significant longitudinal portion of winglet 15. As shown in FIG. 4, key tab 34 bisects chamfers 25b, 25c on winglet 15. Stated otherwise, winglet 15 has left and right-side chamfer edges 12 carrying convexities 25b, 25c. Considered as a complete winglet set, the winglets are arcuately spaced apart on a radial plate (see U-shaped cavity end 9, FIG. 3) and the winglets longitudinally extend from radial sealing plate end 9 thereby forming, when coupled to the female, a male receiving channel 68. When uncoupled, the winglets form a male fence. The fence includes chamfered terminal ends 25-25d. Each winglet is a fence rail and adjacent winglets are separated by an interstitial fence space. In the squared-off embodiment, the winglet fence is four-sided with an upper fence wall, an opposing lower fence wall and a left and right-side fence wall. Also, in the squared-off construct, the female receiving cavity has upper wall laterally spaced from the axial centerline of the female projecting end, the female upper wall has a first and second groove, an opposing lower female wall has opposing first and second grooves, and a left and right-side female wall has facing first and second grooves.

In male coupler 1b, the circumferentially spaced apart arcuate winglets longitudinally extend from the male radial sealing plate 9 towards the proximal male port end facing the female coupler. The plurality of winglets, when coupled, in the female cavity, form a male receiving cavity 68 as a cylindrical fence on the delimiting edge. When not coupled, the winglets form a male fence. The cylindrical winglet male fence is shown in FIGS. 1 and 5. A portion of the to-be-formed male receiving cavity 68 is shown in FIG. 3 and is formed by the radially outboard walls of the winglet male fence. The male bayonet tube segment 94 projects from male gas passage 11. The to-be-formed male receiving cavity 68 is coaxial with the projecting male bayonet tube. When not coupled, the winglet circumferential fence is coaxial with tube 94. See FIGS. 1 and 5.

The present invention utilizes two differentiated gas sealing systems. The primary compressive gas seal is formed by the projecting male bayonet tube 94 which is inserted by the operator into projecting female tube segment 20 (defined by tubular wall 20). This sheathed inserted bayonet tube is the primary compressive gas seal. The secondary compressive gas seal results from the short length arcuate winglets captured at delimiting edge in the female receiving cavity 64, 22a, resulting in the winglets being placed under a tension force which tension force is mechanically transferred to projecting female tube end 4 which is compressed male radial sealing wall 10 forming the base of U-shaped male receiving channel 68 formed by the winglet circumferential fence.

Winglets 15, 31 are arcuately spaced apart by gaps 30 or interstitial regions between each winglet. When the winglets are inserted into female entranceway cavity 22a, 64 and then further longitudinally inserted into the inner female cavity 21, the result is the formation of male receiving cavity 68 which circumferentially locks the couplers simultaneously with male bayonet tube 94 inserted into the female projecting tube 20. The male fence convexities acting on the delimiting edge create a generally circumferentially distributed tension force about the entranceway which draws the bayonet male end into the female projecting end tube and also distributes the compressive force about the periphery of the projecting female end as the same contacts the end stop plate. In the squared-off construction, this peripherally distributed tension force is equally converted into a circumferential compressive force between the projecting female end and the end stop plate. The application of this relatively uniform circumferential compressive force establishes a better gas pressure seal. Further, the key tab in the key slot may present the weakest mechanical element in the gas sealing coupler system because the convexities are not formed on the outboard edges of the key tab. See tab 34, FIG. 1. Hence, the single, bifurcated and trifurcated chamber sets on the key tab carrying winglet is one of the several important aspects of the present invention.

The winglet fence has a radially wider fence mouth or circumference at its proximal end (near the ventilator), a continuously narrower radial throat, which throat leads to secondary compression male seal end surface 10, and a longitudinally inboard stop plate wall 9 (longitudinally inboard from the wider mouth of the to-be-formed male receiving cavity 68). The radial stop plate 9, in the squared-off system, is a lateral plate. The throat of the to-be-formed male cavity 68 terminates at inboard end plate wall 9.

In the illustrated embodiment, male receiving cavity 68 is a truncated U-shaped arcuate cavity (a truncated base stop plate wall 9 forming the conjoining base of the U-shaped channel, one leg of the U-shaped channel being the radially outer wall of the male winglet fence and the other leg being the radially inner wall 22 of female cavity 22a and 21, dependent upon the degree of insertion). The U-shaped channel mouth leads to a radially narrowing throat. The progressively radially narrowing or converging U-shaped throat walls of male receiving cavity 68 form secondary compression male seal surfaces 9, 10 which surfaces are present in all the arcuate winglets. The plate 9 acts as a stop wall for the female projecting end tube 20. The radially narrower, converging U-shaped throat walls form the secondary compression seal. The primary compression seal is formed which is sheathed within the projecting female end defined by wall 20. The projecting female tube 20 may have inboard seal edge 90.

The winglet defined male primary compression seal edge surfaces 9, 10 provide the compression sealing surface for the male receiving cavity and hence a compression seal when projecting female end wall segment 4 is longitudinally forced against throat end wall 9. The compression seal is established by the materials' flexibility. The male and female couplers may be made of the same poly plastic material or the female coupler may be made of a harder material compared to the disposable male coupler (disposable because each patient uses a different breathing head 110 (FIG. 9) and hence the operator must couple different pneumatic lines for each patient).

The main compression sealing surfaces on the inboard coupler end are defined by the sealing coaction of (a) the male bayonet projecting terminal end segment 14 being sheathed by projecting female tube 20; and (b) female cylindrical terminal end 4 acting on the radial cone 10, that is the primary seat at the projecting male bayonet insertion tube 94 in male throat 68. These two compressive systems provide a primary compression seal (the male bayonet in the female sheathing), a secondary compression seal (the female terminus edge 4 against the cone 10).

Alternatively, the female projecting cylindrical terminal end segment 4 may have a slightly continuously radially narrowing sloped exterior surface, or a slightly continuously radially narrowing sloped interior surface, wherein the projecting terminal end segment 4 of female passageway 20 is radially thinned to provide a complementary match with the U-shaped male receiving sealing channel 68.

Another alternate embodiment reverses the male end primary sealing cavity 68 and the female terminal end 4. Stated otherwise, the female outboard coupler body could define winglets and a to-be-formed male receiving channel (similar to male channel 68) and the male coupler could define a projecting cylindrical sheathing tube end (similar to sheathing female end wall segment 20 and female terminus 4).

Each winglet 15, 31 defines, at a longitudinal leading location, a radially protruding arcuate convexity or bump 25. Convexity 25 has a leading chamfer edge 12 and a following chamfer edge 13. The leading edge 12 disposed at the longitudinal outboard terminal edge of winglet 15, 31, and the following chamfer edge 13 being longitudinally inboard of convexity 25.

When the operator inserts the proximal male coupler end into the exterior outboard facing female coupler end, the leading male chamfer edge 12 on convexity 25 enters entranceway 22a, 64, and seats on female delimiting edge 2 between female entranceway receiving cavity 64, 22, and the radially larger female passage 64. When convexity 25 clears edge 2 and the follow-on chamfer is seated delimiting edge 2, winglets 15 and 31 expand radially outward by cam action along the backside of the follow-on male chamfer slope 13 of convexity 25. The term "backside" being inboard of leading chamfer edge 12. The outwardly directed force applied by the male coupler longitudinally pulls the winglet further inboard into the female's larger radial cavity area or cavity 21. The follow-on chamfer edge 13 is captured by a tension fit on delimiting edge 2. The tension fit pulls the male coupler into the female coupler. FIG. 7B shows male winglet 15 locked onto female retaining edge 2. These winglets can also be considered male grappling legs and the convexities acting as grappling hooks which grab the follow-on chamfer surface 13 and maintain the tension force over the length of the winglet. The pulling winglet tension force is transferred into the compressive force by forcing female terminus edge 4 against cone 10.

To further explain the mechanical tension force developed by the winglet legs, is the female coupler has a transitional outboard edge 3 leading to a first circumferential groove 64 which having an entranceway circumference. The longitudinal span of entranceway 64 and the longitudinal span of transitional edge 3 establishes an entranceway longitudinal span, and in FIG. 7B, the entranceway span is longer than the projecting female end 4 distance ("pfed"). If transitional edge 3 was eliminated, the entranceway longitudinal span would be the longitudinal length of cavity 22a (FIG. 3). Winglet 15 has an effective locking distance ("eld") shown in FIG. 7B which is the distance between the base plate end stop 9 and the follow-on chamfer edge 13 of convexity 25. The eld is less than the total longitudinal span of the male fence formed by the winglets (this total fence span being the distance from the terminal end 12 to plate end stop 9 shown in FIG. 1). The winglet fence (FIG. 7B) has a longitudinal fence span that which is less than the projecting female end distance pfed. However, the effective locking distance eld of each winglet is slightly less than the entranceway span of entranceway cavity 64.

Each winglet leg is slightly angled radially outboard and carries a terminal end convexity defining a fence which is circumferentially larger than receiving female entranceway

64. When the winglets and convexities are pushed by the operator into female entranceway 64, the winglets first move radially inward into interstitial spaces and the winglets as a group exert radially outboard forces against the entranceway walls, and, upon full insertion, seat on delimiting edge 2.

The effective locking distance eld of the winglet legs is less than entranceway longitudinal span. When the follow-on chamfer 13 of convexity 25 is seated on delimiting edge 2, the winglet leg is placed in tension by the foreshortened effective locking distance eld of the leg compared to the entranceway longitudinal span. In the illustrated embodiment, the winglet is placed in tension by the foreshortened eld compared to the entranceway plus the transitional edge longitudinal span. Since the effective locking distance or length eld is less than the projecting female end distance pfed, the tension force is transferred from chamfer 13 through the leg structure to the cone 10 which then applies a compression force between cone 10 and terminus edge 4 of projecting female tube 20. The compression force provides another gas seal.

In FIG. 3, the radial sealing plate stop 9 has an opposite plate face which is longitudinally spaced away from a proximal-most radial fin 24. Exposed female coupler edge 7 may be disposed adjacent the proximal-most radial fin 24 when the male coupler is fully inserted in to the female coupler to provide further support to counteract transitional forces applied to the coupler by the operator.

Referring again to the blocking action of non-matching male and female couplers, if the operator attempted to insert a two tab male system 204, FIG. 6B, shown in FIG. 8b as set 204, into the single female slot coupler shown in FIGS. 3 and 4, the trifurcated WC chamfers on terminal end face edge 19 of the two tab male coupler would be blocked by the female terminal end edge 7. A similar blocking action occurs with other non-compatible couplers. FIGS. 6A-6D diagrammatically illustrate end views of complementary male and female couplers. If a single topside key tab was subject to insertion into the two closely set tab-slot configuration 204 (FIG. 6B), the bifurcated topside winglet convexities ("WCs") would be blocked by female coupler edge 7. If the spaced apart two tab-slot configuration 206 (FIG. 6C) was subject to insertion, the topside single WC would be blocked by female edge 7. If the upper and lower opposing single tab-slot configuration 208 (FIG. 6D) was subject to insertion, the lower WCs would be blocked by the lower portions of female edge 7.

Although the illustrated embodiments show an arcuate distribution of winglets, the winglets could be disposed in a square pattern about projecting female tube 20. The winglets would extend longitudinally from radial plate stop 9 extending towards the female coupler. The winglets would be laterally based apart from the axial centerline of male passage 11. The female coupler would have a squared-off female receiving cavity. In this construction, grooves in the outer walls of the female receiving cavity 64, 21, would have a lateral span (spaced of part from the axial centerline 6 of the female coupler) as well as a longitudinal span. The lateral span being normal to and measured from the axial centerline of the female projecting tube 20 to the outer wall defining the female receiving cavities (outer wall similar to wall 22 in FIG. 3). In this sense, the winglets continue to define a male fence about male bayonet 94 as well as female projecting end 20. Of course, different shapes, other than square-shaped female cavity shapes, could be employed and follow the design elements described herein. As used herein, the term "lateral" is positionally established as being normal to the axial centerline of female projecting end tube or the male projecting bayonet tube.

On the female coupling, terminal cylindrical edge 7 is designed to add a second mechanical stopping edge for male fin plate 24. See FIG. 7B. This second mechanical stop may not act as a pressure seal when male key 34 is fit into the complementary female slot 35. These edge interfaces 7, 24 prevent rocking of the fitted coupler system (when the male coupler is fully engaged in the female coupler) and resist transitional forces applied by the operator, thereby preventing a lateral disconnection.

FIG. 7A shows male key tab 34 positioned in female slot 35 and the interstitial space between the slot in the key tab.

The method of coupling either pulsatile gas flow or sensory gas pressure flow from or to a ventilator with a pneumatic line or tube is facilitated by providing a male coupler 1b with a female coupler 1a. The male coupler has a proximal male coupler port, proximal to the ventilator 80 shown in FIG. 9. The male coupler 1b has a distal male coupler port opposite the proximal port, generally at passage end 53 in FIG. 3. The female coupler 1a has an external outboard female port which is external to the ventilator. A key tab is provided on the proximal male port end. The key tab 34 on the proximal male port end matches a key slot on the outboard female port end. The male coupler 1b has a male gas carrying tube 11, fence-formed male grapple legs (referring to winglets 15, 31 and the terminal convexities on the winglets), a male lateral or radial sealing plate 9, and a unique extending key tab configuration. These key tab configurations are shown in connection with FIGS. 6A-D and 8A-D as configurations 202a, 204a, 206a and 208a. The female coupler has a female gas carrying tube 6, a radially or laterally narrow female entranceway 64, a radially or laterally larger female coupling chamber 21, a female gas carrying terminal end 20, and a unique key slot configuration such as configurations 202a, 204a, 206a and 208a. The female coupler is installed in the ventilator (see FIG. 9) and passes pulsatile gas flow or sensory gas pressure flow from or to the ventilator to the outboard female port. On the male coupler, spaced apart primary and secondary compressive conically forced seals are provided by frustoconical element 26, transitory edge 27, and frustoconical structures 17, 28 and 29. These first and second compressive conically forced seals are established between the distal male coupler port and the pneumatic line or tube.

Simultaneous with the insertion of the unique male extending key configuration into the unique key slot configuration, the male gas carrying tube 94 is bayoneted into the female gas carrying tube 20 by sheathing the male tube with the female tube and conjoining the male and female gas passages 11, 6. As explained earlier, male bayoneted tube 94 on the projecting female terminal end 20 provides an initial pressure seal as a first compressive gas seal. Simultaneous with insertion of the male key tab into the female key slot, the operation forces the radially larger fence-formed male grapple legs, that is, the winglets carrying the terminal convexities, into the radially narrower female entranceway 64 (see FIG. 7B). By grappling the convexity carrying grapple legs onto the female catch surfaces 2 (see FIG. 7B with follow-on chamfers on delimiting edge 2), the grapple legs catch on and are maintained on the catch surface edge 2.

Again, simultaneous with the grappling, the male grappling legs, are placed under tension force because the effective locking distance eld is slightly shorter than the entranceway longitudinal span. The projecting female end distance or span pfed is shorter than entranceway 64 plus the longitudinal span of transition slope 3 (FIG. 3) and the effective locking distance eld of the winglets or the grappling legs. The method converts tension force in the grappling legs into a compressive force applied between the male sealing plate and the female terminal end 5. This gas compression interface is the second gas compressive seal between the male coupler and the female coupler. The male coupler and the female coupler can be coupled and decoupled thereby pneumatically coupling the line from or to the ventilator and passing pulsatile gas flow or sensory gas pressure flow to and from the ventilator through the female and the male coupler into and from the pneumatics lines.

In a preferred embodiment, the male and the female couplers are made of suitable plastic. To ensure that the pneumatic lines carrying pulsatile gas and sensory pressure gas do not disengage from the ventilator control-monitor, the couplers must remain connected together such that a longitudinal "pull off" force does not decouple the pressure lines from the ventilator.

In a preferred embodiment, the longitudinal span of the male coupler is about 1 inch in length. Similarly, the female coupler is about 1 inch in length. In a preferred embodiment, the breathing head 110 is connected to the pneumatic line 60 by the manufacturer and the head plus line system is delivered to the operator. The tab longitudinal span is about 0.125 inches in length (no longer than 0.25 inches), its radial outboard extension span of the tab is about 0.125 inches (no longer than 0.25 inches), and the diameter of male fence is about 0.375 inches (no more than 0.5 inches). The dimensions of the coupler are related to the inner and out diameters of the pulsatile gas supply line and the sensory pressure line. Typical high pressures in the pulsatile gas supply line are between 0-30 psi and typical sensory gas pressures are between 0-2 psi. Typical high pressures in the nebulizer supply line 122 are between 0-55 psi.

FIG. 9 diagrammatically illustrates breathing head 110 pneumatically coupled to ventilator 80. The ventilator operates to supply gas to breathing head 110 (a controlled gas flow generated by the ventilator), and as a monitoring device, sensing gas pressure P from the breathing head. For these reasons, the male-female couplers described herein are critical to the respiratory operation of the ventilator system (the ventilator control-monitor and the breathing head). Breathing head 110 has a distal end 114 receiving the pulsatile gas and an opposite proximal end 116. Breathing head 110 includes, at its distal end, an optional mouthpiece 118. Tube 119 is an extension from the exhalation port of the breathing head. In the illustration, breathing head 110 includes an elongated view passage 112 and a depending body segment 123 leading to nebulizer container 120. A continuous gas supply line 122 is attached to nebulizer 120. A pulsatile gas supply line 124 is connected to an end cap at the proximal end 116 of breathing head 110. Pneumatic sensory line 126 (carrying pressure P as a pneumatic sensory signal), is coupled at one end to a gas sensor port on the breathing head 110 and is coupled, at the other end, to the ventilator gas supply control-monitor 80. Pneumatic sensory line 126 carrying pressure P permits the ventilator to measure gas pressure P in the breathing head 110. For further details of the operation of the breathing head 110, reference is made to patent application Ser. No. 16/391,481, filed Apr. 23, 2019, the contents of which is incorporated herein by reference thereto.

It should be noted that the breathing head illustrated in FIG. 9 is only one of several different breathing heads which are used in connection with the delivery of pulsatile gas, via a breathing head, to the patient and which is operable with a ventilator control-monitor which (a) generates the pulsatile gas, (b) controls the delivery of the pulsatile gas to the breathing head and to the patient, and (c) obtains a sensory, pneumatic pressure signal P from the breathing head indicating critical pressures in an internal chamber in the breathing head. This pneumatic pressure signal P is a feedback signal utilized in control of the delivery of pulsatile gas by the ventilator. The monitoring of pressure P in the breathing head is critical in controlling the delivery of pulsatile gas, the frequency of the pulsatile gas generated by the ventilator and delivered through pulsatile gas supply line 124 to the breathing head, the peak pressures of the pulsatile gas and, to some extent, the volume of pulsatile gas supplied through the breathing head to the patient.

The claims appended hereto are meant to cover modifications and changes within the scope and spirit of the present invention.

What is claimed is:

1. In combination with a ventilator generating pulsatile gas through a pulsatile gas outlet and sensing a sensory gas pressure at a pneumatic sensory input, a coupler system adapted to be interposed between the ventilator and a pneumatic line or tube, the coupler system pneumatically coupled to either the pulsatile gas outlet or the sensory input, the coupler system comprising:

a male coupler having male coupler body with a proximal male port end and an opposing distal male port end, the male coupler body having a longitudinal gaseous male passageway between the proximal and distal male port ends;

a complementary female coupler removably interlockable with the male coupler;

the female coupler having a female coupler body;

the female coupler body having:

a longitudinal gaseous female passageway from an outboard facing female port end to an interior ventilator female port opposite the female port end, the interior ventilator female port adapted to be pneumatically coupled to either the pulsatile gas outlet or the sensory input, the female port end adapted to be exteriorly outboard of the ventilator;

a cylindrical female receiving cavity in the female coupler body at the female port end, the female receiving cavity defined between a radially inner female receiving wall on the female coupler body and a projecting cylindrical female end portion, the projecting female end being an extension of the gaseous female passageway and being coaxially disposed within and projecting through the female receiving cavity, the projecting female end having a female terminus edge;

at least one radial primary key slot in the inner female receiving wall which at least one key slot extends from the female receiving cavity either fully or partly through the inner female receiving wall, the at least one key slot being colinear with the projecting female end;

a radially widening sloped transitional female edge on inner female receiving wall at the female terminal end;

first and second circumferential grooves on the inner female receiving wall, the first groove interposed between the sloped transitional female edge and the second groove, a delimiting edge at the intersection of the first and second grooves, the first groove having an entranceway circumference and an entranceway longitudinal span;

the male coupler body having:

a frustoconical primary outboard port male seal formed at a distal end of the gaseous male passageway;

a frustoconical secondary outboard port male seal, the secondary outboard port seal being longitudinally inboard the primary outboard port male seal, the primary and secondary outboard port male seals adapted to pneumatically connect the pneumatic line or tube to the gaseous male passageway;

a projecting bayonet insertion tube terminating at the proximal male end as an extension of the gaseous male passageway, the bayonet tube sized to sheathe within the projecting female end;

a radial sealing plate;

a plurality of circumferentially spaced apart arcuate winglets longitudinally extending from the sealing plate towards the proximal male port end, the plurality of winglets forming a male cylindrical fence, the bayonet tube coaxial in the cylindrical fence, an effective locking longitudinal winglet length being less than the entranceway span, the male cylindrical fence having a longitudinal fence depth, the longitudinal cavity depth being less than the projecting female end;

each winglet of the plurality of winglets having a radially outward leading edge convexity at its terminal winglet end, a longitudinally inboard convexity surface defining an outboard end of the effective locking length and the sealing plate defining an inboard end of the effective locking length;

wherein the plurality of winglets define a plurality of convexities at a plurality of terminal winglet ends, the plurality of convexities defining a fenced circumference which is greater than the entranceway circumference;

at least one radially extending primary key tab on at least one winglet of the plurality of winglets, the at least one key tab collinear with the bayonet tube and the cylindrical fence, the at least one radially extending primary key tab bisecting the corresponding convexity on the at least one winglet, the at least one key tab being insertably complementary to the at least one key slot;

wherein the plurality of winglets move radially inward due to the fenced circumference being greater than the entranceway circumference and, upon coaction of the plurality of convexities on the delimiting edge, the plurality of winglets placed in tension due to the effective locking length being less than the entranceway span and the female terminus edge being placed in sealing compression against the radial sealing plate due to the longitudinal cavity depth being less than the projecting female end.

2. The coupler system combination as claimed in claim 1 wherein the bayonet tube receivable in the projecting female end and the sheathed bayonet tube in the projecting female end forms a primary pressure seal for the coupler system and the sealing compression between the female terminus edge and the radial sealing plate forms a secondary pressure seal for the coupler system.

3. The coupler system combination as claimed in claim 2 wherein the bayonet tube has a frustoconical bayonet shape with a radially narrow bayonet terminus end wherein application of either pulsatile gas or the sensory gas pressure in the gaseous male passageway increases the primary pressure seal due to the frustoconical bayonet shape sheathed in the projecting female end.

4. The coupler system combination as claimed in claim 1 wherein the radial span of the delimiting edge is greater than the fenced circumference.

5. The coupler system combination as claimed in claim 1 wherein the sloped transitional female edge is chamfered to accept the fenced circumference, the sloped transitional female edge having a transitional female edge longitudinal span, the entranceway span defined both by the transitional female edge longitudinal span and the entranceway longitudinal span of the first groove.

6. The coupler system combination as claimed in claim 1 wherein the male coupler body is an elongated male coupler body with a plurality of radial fins protruding radially outboard from the male gaseous passageway, the plurality of radial fins being intermediate the secondary outboard port male seal and the proximal male end.

7. The coupler system combination as claimed in claim 6 wherein the radial sealing plate has a plate face which is placed in sealing compression with the female terminus edge, the radial sealing plate has a longitudinal outboard plate face, the plurality of radial fins has a proximal-most radial fin which is longitudinally spaced apart from the outboard plate face.

8. The coupler system combination as claimed in claim 7 the female receiving cavity having a radially outer wall, the female receiving cavity having a longitudinal female receiving cavity span encompassing the transitional female edge and the first and second grooves, the longitudinal female receiving cavity span being substantially equivalent to or nominally longer than a male longitudinal span from the proximal-most radial fin to a proximal male port terminus, thereby forming a tertiary pressure seal for the coupler system due to the longitudinal female receiving cavity span being longer than the male longitudinal span when the plurality of winglets are placed in tension due to the effective locking length being less than the entranceway span.

9. The coupler system combination as claimed in claim 1 wherein the at least one radial primary key slot is a first key slot and the at least one radial primary key tab on the at least one winglet is a first key tab on a first winglet, the inner female receiving wall having a second key slot, the plurality of winglets having a second winglet, the second winglet having a second key tab collinear with the axial centerline through the bayonet tube and the cylindrical fence and the second key tab being insertably complementary to the second key slot.

10. In combination with a ventilator generating pulsatile gas through a pulsatile gas outlet and sensing a sensory gas pressure at a pneumatic sensory input, a coupler system adapted to be interposed between the ventilator and a pneumatic line or tube, the coupler system pneumatically coupled to either the pulsatile gas outlet or the sensory input, the coupler system comprising:

a male coupler having male coupler body with a proximal male port end and an opposing distal male port end, the male coupler body having a gaseous male passageway between the proximal and distal male port ends;

a complementary female coupler removably interlockable with the male coupler;

the female coupler having a female coupler body;

the female coupler body having:

a gaseous female passageway from an outboard exterior female port to an interior ventilator port opposite the female port, the ventilator port adapted to accept pulsatile gas or sensory gas pressure;

a female receiving cavity at the female port defined between a laterally inner female receiving wall system and a projecting cylindrical female end, the projecting female end an extension of the gaseous female passageway and projecting through the female receiving cavity and having a female terminus edge;

at least one primary key slot in the inner female receiving wall system which extends either fully or partly from the female receiving cavity, the at least one key slot being colinear with the projecting female end;

a transitional female edge on the inner female receiving wall system;

first and second grooves on the inner female receiving wall system, the first groove interposed between the transitional female edge and the second groove, a delimiting edge between the first and second grooves, the first groove having an entranceway lateral span and an entranceway longitudinal span;

the male coupler body having:

a frustoconical primary outboard port male seal formed at a distal end of the gaseous male passageway;

a frustoconical secondary outboard port male seal, the secondary outboard port seal being longitudinally inboard the primary outboard port male seal, the primary and secondary outboard port male seals adapted to pneumatically connect the pneumatic line or tube to the gaseous male passageway;

a projecting bayonet cylindrical insertion tube as an extension of the gaseous male passageway, the bayonet tube removably sheathed within the projecting female end;

a laterally extending sealing plate normal to the bayonet tube;

a plurality of spaced apart winglets spaced apart from and disposed about the bayonet tube, the plurality of winglets longitudinally extending from the sealing plate towards the proximal male port end, the plurality of winglets forming a male fence about the bayonet tube, an effective locking longitudinal winglet length being less than the entranceway longitudinal span, the male fence having a longitudinal fence depth being less than the projecting female end;

each winglet having one or more terminal end outward leading edge catch surfaces, the one or more catch surfaces defining an outboard end of the effective locking length and the sealing plate defining an inboard end of the effective locking length;

the plurality of catch surfaces of the male fence defining a fenced lateral span which is greater than the entranceway lateral span;

at least one laterally extending primary key tab on at least one winglet collinear with the bayonet tube, the at least one key tab being insertably complementary to the at least one key slot;

wherein the plurality of winglets move laterally inward due to the fenced lateral span being greater than the entranceway lateral span and upon coaction of the plurality of catch surfaces on the delimiting edge the plurality of winglets placed in tension due to the effective locking length being less than the entranceway longitudinal span and the female terminus edge being placed in sealing compression against the lateral sealing plate due to the longitudinal cavity depth being less than the projecting female end.

11. The coupler system combination as claimed in claim 10 wherein the at least one primary key slot is a first key slot and the at least one primary key tab on the at least one winglet is a first key tab on a first winglet, the inner female receiving wall having a second key slot, the plurality of winglets having a second winglet, the second winglet having a second key tab collinear with the axial centerline through the bayonet tube and the second key tab being insertably complementary to the second key slot.

12. The coupler system combination as claimed in claim 10 wherein the bayonet tube has a frustoconical bayonet shape with a radially narrow bayonet terminus end wherein application of either pulsatile gas or the sensory gas pressure in the gaseous male passageway increases the primary pressure seal due to the frustoconical bayonet shape sheathed in the projecting female end.

13. The coupler system combination as claimed in claim 10 wherein the transitional female edge is either chamfered or sloped to accept the male fence, the chamfered or sloped transitional female edge having a transitional female edge longitudinal span, the entranceway span defined both by the transitional female edge longitudinal span and the entranceway longitudinal span of the first groove.

14. The coupler system combination as claimed in claim 10 wherein the male coupler body is an elongated male coupler body with a plurality of radial fins protruding radially outboard from the male gaseous passageway, the plurality of radial fins being intermediate the secondary outboard port male seal and the proximal male end.

15. The coupler system combination as claimed in claim 14 wherein the radial fins has at least one longitudinal plate support disposed in at least one interstitial space between at least two adjacent radial fins, the longitudinal plate support being collinear with an axial centerline through the gaseous male passageway.

16. A method of coupling either a pulsatile gas flow or a sensory gas pressure from or to a ventilator with a pneumatic line or tube comprising:

providing a male coupler interlockable with a female coupler, the male coupler having a proximal male coupler port proximal to the ventilator and a distal male coupler port distal to the ventilator, the female coupler having an external outboard female port external to the ventilator;

providing a key on the proximal male port and providing a matching key slot in the outboard female port;

providing the male coupler with a male gas carrying tube, fence-formed male grapple legs, a male sealing plate, and a unique extending key configuration;

providing the female coupler with female gas carrying tube, a radially or laterally narrow female entranceway, a radially or laterally larger female coupling chamber, a female catch surface delimiting the female entranceway and the female coupling chamber, a female gas carrying tube terminal end, and a unique key slot configuration;

wherein the fence-formed male grapple legs have a greater radial or lateral span than the narrow female entranceway;

installing the female coupler on the ventilator and passing the pulsatile gas flow or sensory gas pressure from or to the ventilator via the outboard female port;

establishing spaced apart primary and secondary compressive conically forced seals between the distal male coupler port and the pneumatic line or tube, both conically forced seals acting on the pneumatic line or tube;

simultaneous with inserting the unique male extending key into the unique key slot:

bayoneting portions of the male gas carrying tube into the female gas carrying tube by sheathing the male tube with the female tube and conjoining the male and female gas passages;

establishing a first compressive gas seal by bayoneting and sheathing the male coupler to the female coupler;

forcing the fence-formed male grapple legs with the greater radial or lateral span into the radially or laterally narrow female entranceway;

grappling the male legs onto the female catch surface;

simultaneous with grappling the male legs onto the catch surface, placing the male legs under constant tension force;

converting the tension force to a compressive force applied between the male sealing plate and the female tube terminal end and thereby establishing a second gas compressive seal between the male coupler and the female coupler; and removably coupling and decoupling the proximal male port to the outboard female port thereby coupling and decoupling of the pneumatic line or tube to the ventilator and, when coupled, passing the pulsatile gas flow or sensory gas pressure from or to the ventilator, through the female coupler and the male coupler.

17. The method as claimed in claim 16 including establishing the constant tension force by longitudinally foreshortening the fence-forming male legs compared to a sheathed portion of the female tube.

18. The method as claimed in claim 16 wherein the female coupler is a first female coupler have a first key slot configuration, the male extending key configuration is a male extending key configuration which can be inserted into the first key slot configuration;

providing a second female coupler have a second key slot configuration which is positionally different than the first key slot configuration;

blocking bayonetting and sheathing of the male extending key into the second key slot by male grapple legs impacting the radially narrow female entranceway.

\* \* \* \* \*